(12) United States Patent
Crites-Bachert (10) Patent No.: US 11,937,958 B1
(45) Date of Patent: *Mar. 26, 2024

(54) METHOD FOR NEEDLE POSITIONING AND LEAD IMPLANTATION FOR SACRAL NEUROMODULATION

(71) Applicant: Melanie Crites-Bachert, Gresham, OR (US)

(72) Inventor: Melanie Crites-Bachert, Gresham, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/465,988

(22) Filed: Sep. 3, 2021

Related U.S. Application Data

(63) Continuation of application No. 16/503,938, filed on Jul. 5, 2019, now Pat. No. 11,109,821.

(60) Provisional application No. 62/694,772, filed on Jul. 6, 2018.

(51) Int. Cl.
*A61B 6/00* (2006.01)
*A61B 6/12* (2006.01)
*A61B 90/00* (2016.01)

(52) U.S. Cl.
CPC ............... *A61B 6/12* (2013.01); *A61B 6/487* (2013.01); *A61B 90/39* (2016.02); *A61B 2090/3908* (2016.02); *A61B 2090/395* (2016.02)

(58) Field of Classification Search
CPC ....................................................... A61B 6/12
See application file for complete search history.

*Primary Examiner* — Joseph M Santos Rodriguez
(74) *Attorney, Agent, or Firm* — Fleit Intellectual Property Law; Jon Gibbons; Paul Bianco (57) ABSTRACT

A method for needle positioning for lead implantation for sacral neuromodulation uses fluoroscopy to locate anatomical landmarks. Markings on the skin of the patient are made to determine optimal positioning of a foramen needle used to position the leads and electrodes of an implantable electrical stimulator.

10 Claims, 8 Drawing Sheets

METHOD FOR NEEDLE POSITIONING AND LEAD IMPLANTATION FOR SACRAL NEUROMODULATION

FIELD OF THE DISCLOSURE

The disclosure relates to a method for needle positioning and lead implantation for sacral neuromodulation.

BACKGROUND

Electrical stimulation of somatic afferent pathways in the sacral spinal roots (as well as the pudendal nerve or posterior tibial nerve) can inhibit bladder activity in both humans and animals and is clinically effective in treating overactive bladder symptoms. Stimulation of the sacral S3 spinal root is currently an FDA approved therapy for the lower urinary tract disorders including bladder overactivity, urgency, frequency, incontinence, and urinary retention. Stimulation is also an FDA approved therapy for bowel control. Although the mechanisms underlying neuromodulation are not totally understood, this type of therapy has become popular because bowel control and lower urinary tract dysfunctions in some patients are difficult to manage with medication.

Sacral neuromodulation requires an invasive (albeit a minimally invasive) procedure to implant a stimulator (e.g., InterStim®, Medtronic Inc.) and electrodes, which are also referred to as the leads. While the implantable stimulators and leads have been engineered and designed for efficiency, the success of the clinical outcome still depends heavily on the surgical technique. It requires skilled medical staff to insert the needle for optimal lead position relative to the nerve. Thus, current neuromodulation treatments can be effective to suppress bladder overactivity and bowel control, but only if the proper surgical technique is observed.

Because of the expense and inconvenience of the procedure, many individuals that could potentially benefit from sacral neuromodulation do not consider sacral neuromodulation in light of the variable outcome and the potential added complications if an additional procedure is necessary to improve the clinical outcome that the first procedure failed to achieve. Thus, there exists a need for an improved method for needle positioning and lead implantation for sacral neuromodulation.

SUMMARY OF THE DISCLOSURE

The disclosed method is for positioning a foramen needle to implant a lead of an electrical stimulator for sacral neuromodulation of a patient. In one embodiment, the method comprises: visualizing with fluoroscopy an anterior/posterior view of the sacrum and sacroiliac joints of the patient; marking on the skin of the patient a midline of the sacrum vertically and a horizontal line from one sacroiliac joint to the other sacroiliac joint; marking a first point on the horizontal line located a first distance in a first lateral direction from the sacral midline, wherein the first distance approximates a first midline of a desired sacral foramen; locating the first midline of the desired sacral foramen using the fluoroscopic anterior/posterior view and the first point and marking the skin of the patient with a first midline vertical line; marking the skin of the patient at a second distance and a third distance from the horizontal line superiorly on the first midline vertical line, thereby approximating where the desired foramen should be located to place the needle; marking the skin of the patient with a first medial vertical line representing the medial portion of the first sacral edge using the fluoroscopic anterior/posterior view; locating the desired sacral foramen with fluoroscopy in a lateral view; and placing the needle through the skin at an angle using the skin markings at one of the second and third markings, beginning medially at the first midline vertical line and progressing laterally to the first medial vertical line until a distal end of the needle drops into the desired sacral foramen.

The disclosed method can also include: marking a second point on the horizontal line located the first distance in a second lateral direction from the sacral midline; locating a second midline of another desired sacral foramen using the fluoroscopic anterior/posterior view and the second point and marking the skin of the patient with a second midline vertical line, the another desired sacral foramen opposite the desired sacral foramen; marking the skin of the patient at the second distance and the third distance from the horizontal line superiorly on the second midline vertical line, thereby approximating where the another desired foramen should be located to place the needle; and marking the skin of the patient with a second medial vertical line representing the medial portion of the second sacral edge using the fluoroscopic anterior/posterior view.

In an embodiment, the needle angle is approximately 45 degrees. However, the needle angle is varied depending on the body habitus of the patient. The placing of the needle can be done under fluoroscopic visualization.

In an exemplary embodiment, after the distal end of the needle drops into the desired sacral foramen, the angle of the needle is adjusted until the needle is 1 cm from the inferior edge of the desired sacral foramen and parallel to the inferior edge of the desired sacral foramen. The angle of the needle can be adjusted using the fluoroscopic anterior/posterior view until the needle is parallel to the first medial vertical line.

In order to confirm placement of the needle, electricity can be conducted through the needle. In this regard, the angle of the needle can be adjusted until the patient exhibits a desired response with the conducting of electricity through the needle.

For some clinical situations, the first distance is 2 cm, the second distance is 4 cm, and the third distance is 5 cm.

Another aspect of the disclosure relates to a method for positioning a foramen needle to implant a lead of an electrical stimulator for sacral neuromodulation of a patient. The disclosed method comprises:
 1. visualizing with fluoroscopy an anterior/posterior view of the sacrum and sacroiliac joints of the patient;
 2. marking on the skin of the patient a midline of the sacrum vertically and a horizontal line from one sacroiliac joint to the other sacroiliac joint;
 3. marking a first point on the horizontal line 2 cm in a first lateral direction from the sacral midline and a second point on the horizontal line 2 cm in a second lateral direction from the sacral midline;
 4. locating a first midline of a desired sacral foramen using the fluoroscopic anterior/posterior view and the first point and marking the skin of the patient with a first midline vertical line;
 5. locating a second midline of another desired sacral foramen using the fluoroscopic anterior/posterior view and the second point and marking the skin of the patient with a second midline vertical line, the another desired sacral foramen opposite the desired sacral foramen;
 6. marking the skin of the patient at 4 cm and 5 cm from the horizontal line superiorly on the first midline vertical line, thereby approximating where the desired foramen should be located to place the needle;
7. marking the skin of the patient at 4 cm and 5 cm from the horizontal line superiorly on the second midline vertical line, thereby approximating where the another desired foramen should be located to place the needle;
8. marking the skin of the patient with a first medial vertical line representing the medial portion of the first sacral edge using the fluoroscopic anterior/posterior view;
9. marking the skin of the patient with a second medial vertical line representing the medial portion of the second sacral edge using the fluoroscopic anterior/posterior view;
10. locating the desired sacral foramen with fluoroscopy in a lateral view; and
11. placing the needle through the skin at an angle using the skin markings at one of the 4 cm and 5 cm markings, beginning medially at the first midline vertical line and progressing laterally to the first medial vertical line until a distal end of the needle drops into the desired sacral foramen.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

As required, embodiments are disclosed herein; however, it is to be understood that the disclosed embodiments are merely examples and that the methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

Figure 1:
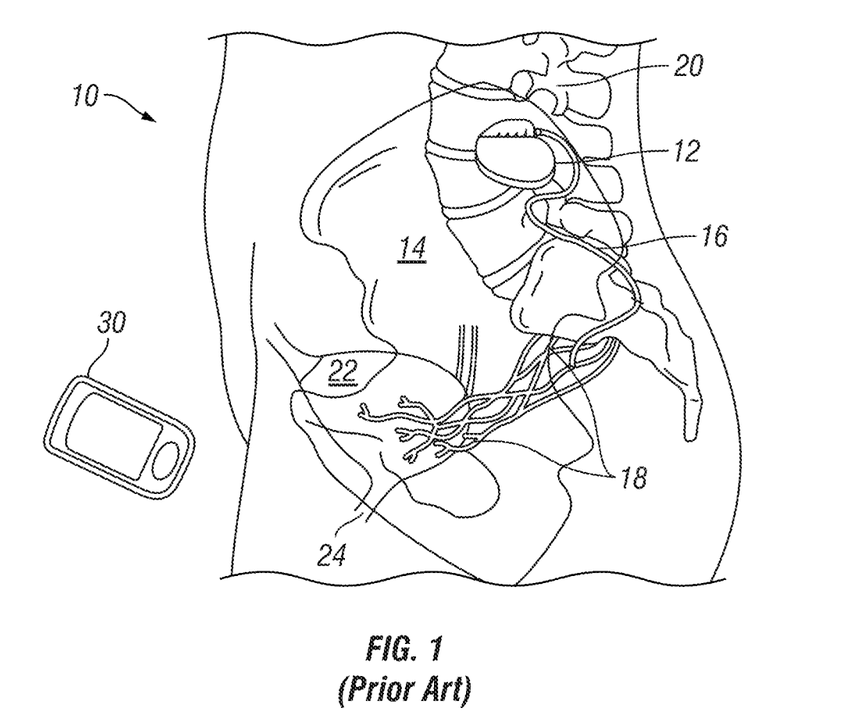
FIG. 1 is a schematic illustration showing a conventional sacral nerve stimulator system.
Figure 2:
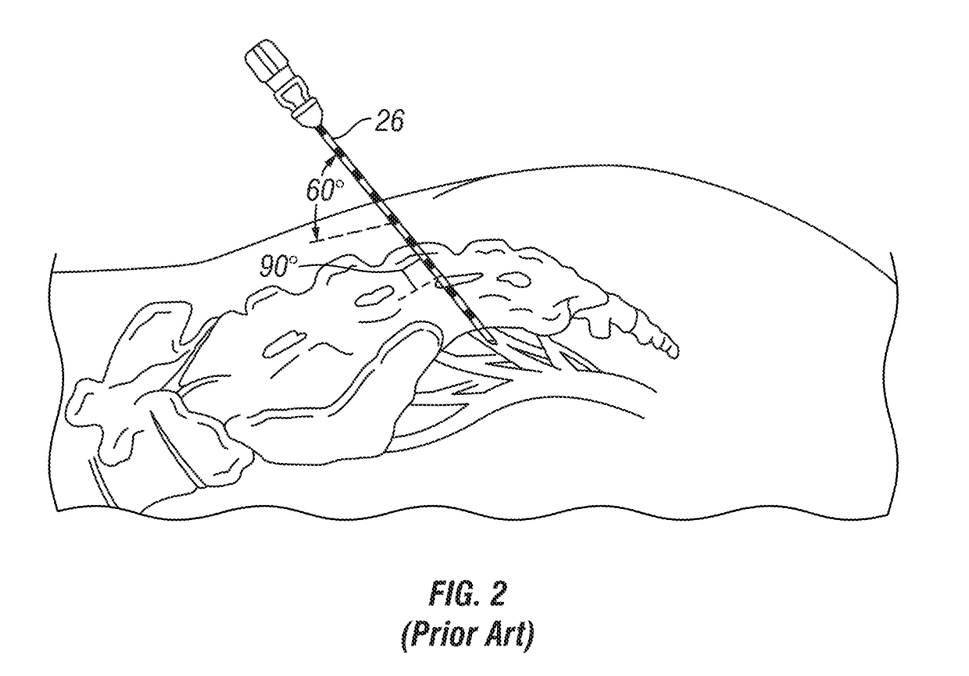
FIG. 2 is a schematic illustration showing needle positioning.

FIG. 1 shows a conventional sacral nerve stimulator system 10. System 10 includes an implant (stimulator) 12 which is implanted proximal the patient's iliac crest 14 and a wire lead (having one or more electrodes) 16 which extends from implant 12 to the sacral nerves 18 that emerge from the spine 20 to control, among other things, urinary function of the bladder 22 and urethra 24. The electrodes at the distal end of the wire lead 16 are positioned proximal the sacral nerves 18 using a foramen needle 26. FIG. 2 shows needle 26 inserted through a foramen 28. After the distal end of the wire lead 16 is positioned, a tunneller is inserted through the puncture wound created by foramen needle 26 to subcutaneously extend wire lead 16 to stimulator 12. Thus, stimulator 12 and wire lead 16 are completely implanted. An external control 30 is used to program or control the delivery of electrical pulses to sacral nerves 18 from implant 12 through wire lead 16.

With reference to FIGS. 1-9, an embodiment of the disclosed methods for needle positioning and lead implantation for sacral neuromodulation is now described.

As is well known, the patient is positioned prone on the procedure table with bolsters to make the patient's sacrum flat on the table. The patient is prepped and draped in a conventional manner.

Figure 3:
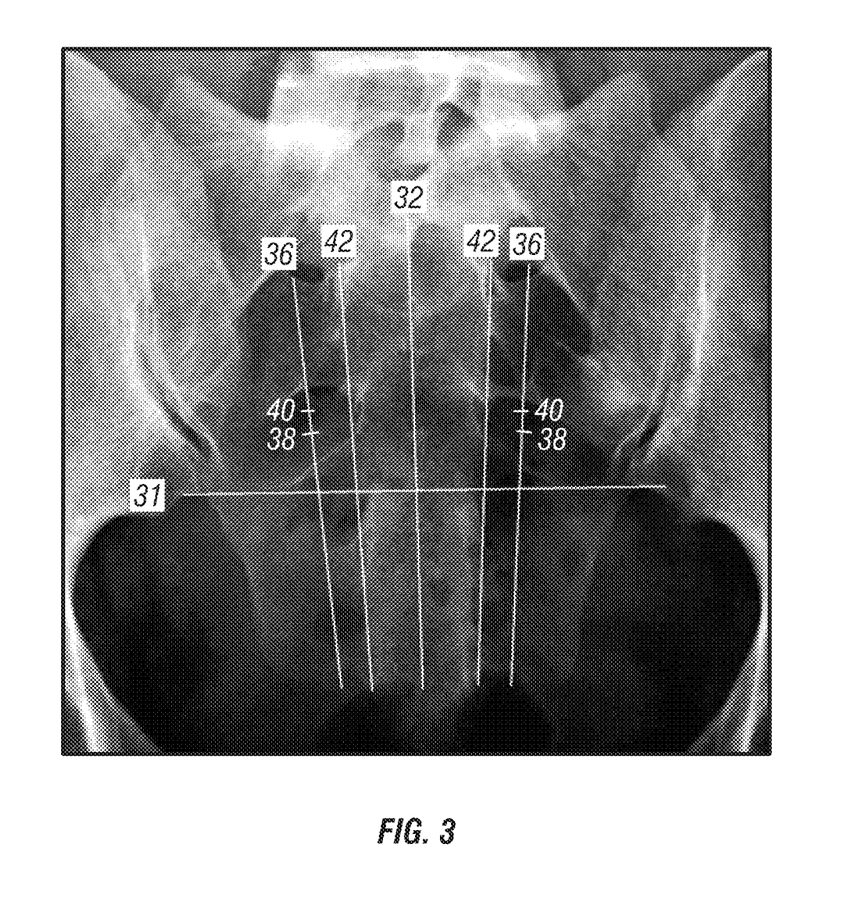
FIG. 3 is an anterior-posterior fluoroscopic image of the sacrum showing lines and markings made according to the disclosed method.
Figure 9:
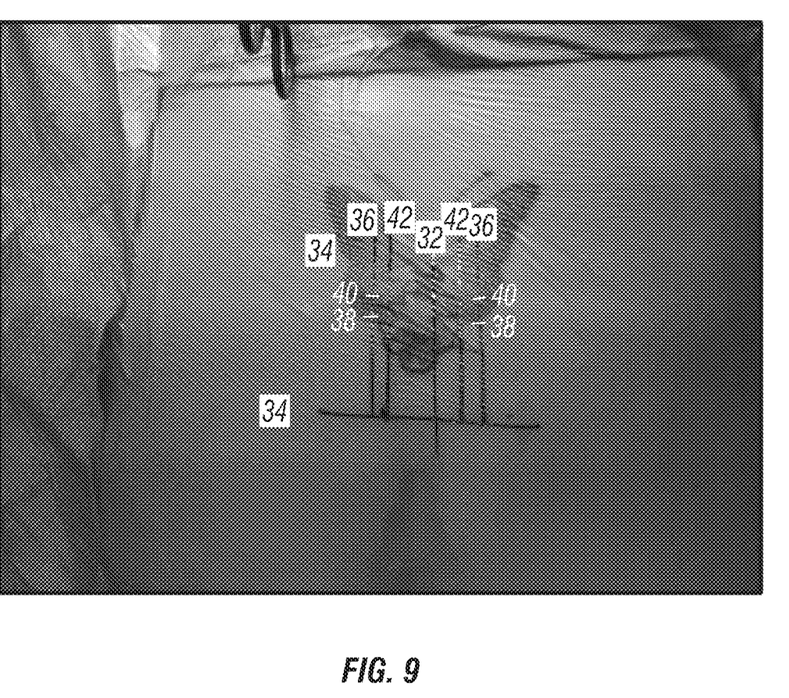
FIG. 9 is a photograph showing skin markings made according to the disclosed method.

Under fluoroscopy in the Anterior/Posterior view, the practitioner marks the midline of the sacrum vertically 32 and the sacroiliac joints horizontally 34 on the patient's skin. FIG. 3 shows lines 32, 34 on the fluoroscopic image on the computer monitor and FIG. 9 shows lines 32, 34 made on the skin of the patient. Any suitable marker or similar implement can be used to make the lines and/or marks. If desired, a straight edge can be used in making the lines and/or marks.

Following horizontal line 34, the practitioner measures and marks 2 cm on the skin from vertical line 32 to give an approximation of where to begin to find the foraminal midline. As one of ordinary skill in the art will appreciate, 2 cm is chosen since this distance is an approximation for the human sacrum (based on standard anatomical sizes) to provide a starting point for where to begin finding the foraminal midline of S2, S3, or S4. The disclosure contemplates that the practitioner can deviate from 2 cm (for example, if the patient is of small or large stature). The disclosure also contemplates that a distance other than 2 cm can be used for other clinical situations (e.g. lumbar neuromodulation).

It should be noted that any skin markings as disclosed herein do not necessarily correlate to the exact distance appearing on fluoroscopy as there is space between the skin and actual sacrum secondary to tissue. The concept is to measure on the skin for an approximation of where to find the sacral #3 foramen fluoroscopically. The needle is passed through sacral #3 foramen for lead placement. The sacral #3 foramen is selected as it generally provides access to the sacral spinal nerve #3, which is targeted for bladder and bowel control. In some individuals, other sacral foramen (e.g. sacral #2 foramen or sacral #4 foramen) provide better access to the sacral spinal nerve #3. In other cases as previously noted, a different nerve may be selected for neuromodulation. Accordingly, the present disclosure contemplates access through other foramen and neuromodulations of other nerves.

Using fluoroscopy in the Anterior/Posterior view and the 2 cm markings, the practitioner finds the midline of the sacral foramen #3 bilaterally and draws a vertical line 36 at the midline of sacral foramen #3 bilaterally on the skin. Although the figures and this detailed description show and describe bilaterally location, the disclosure contemplates unilateral location, i.e. marking on one side of the spine. Subject to anatomical variation vertical line 36 is parallel to vertical line 32.

The practitioner makes a skin marking at 4 cm (marking 38) and 5 cm (marking 40) from horizontal line 34 superiorly bilaterally on vertical line 36 to give an approximation of where the foramen should be located to place the needle. The disclosure contemplates that the practitioner can deviate from 4 cm and/or 5 cm (for example, if the patient is of small or large stature). The disclosure also contemplates that distances other than 4 cm and/or 5 cm can be used for other clinical situations (e.g. lumbar neuromodulation).

Using fluoroscopy in the Anterior/Posterior view, the practitioner vertically marks the medial portion of the sacral edge bilaterally (line 42).

Line 42 indicates the absolute medial aspect of the sacrum for which the needle can be placed and line 36 indicates the near-absolute lateral aspect for which the Sacral #3 nerve will be located. This provides an anterior/posterior guideline for needle placement while changing needle angle placement in the lateral view.

Figure 4:
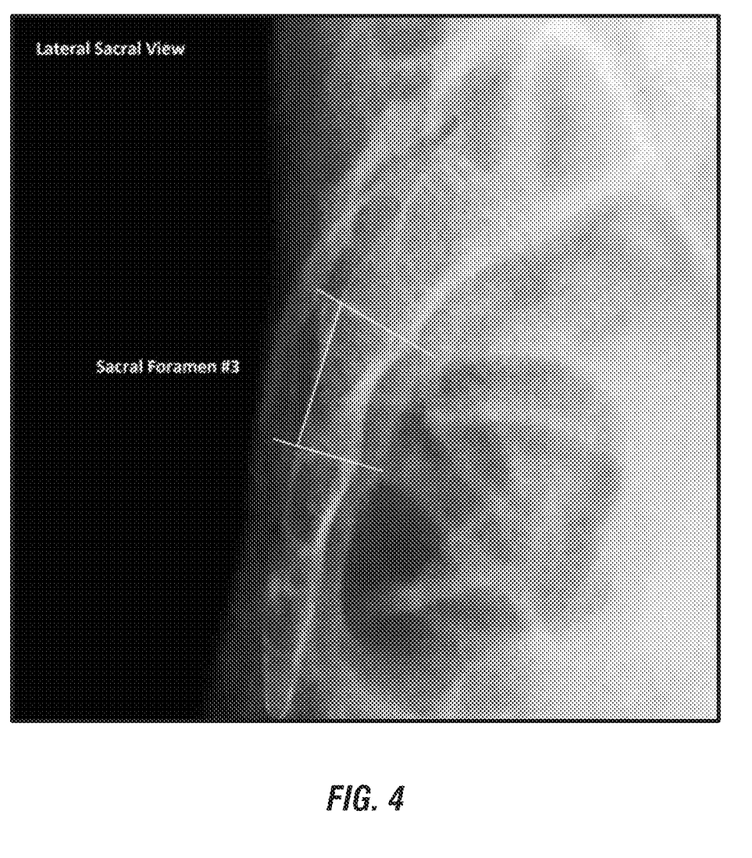
FIG. 4 is a lateral fluoroscopic image of the sacrum showing lines and markings made according to the disclosed method.

As shown in FIG. 4, in the lateral fluoroscopic view, the practitioner finds the sacral #3 foramen visually. The practitioner then begins placing needle through the skin at an approximately 45-degree angle using the skin markings in the anterior view at the 4 cm (marking 38) or 5 cm (marking 40) markings beginning medially (using line 42 as a landmark) and progressing to the most lateral edge (using line 36 as a landmark) until the needle drops into the sacral #3 foramen. The needle angle insertion may be varied depending on the patient's body habitus. The practitioner confirms this placement in the lateral fluoroscopic view and adjusts the angle with minute movements of the needle until the needle is 1 cm from the inferior edge of sacral foramen #3 and parallel to the inferior edge of sacral foramen #3. Needle 26 is schematically shown in this position in FIG. 5.

Figure 5:
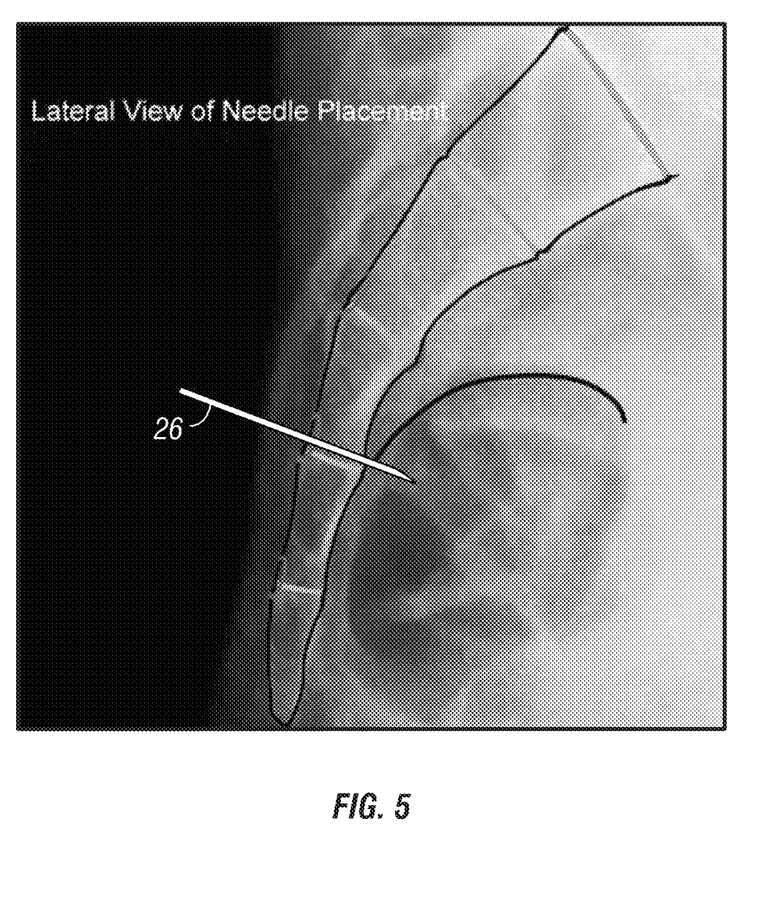
FIG. 5 is a lateral fluoroscopic image of the sacrum showing optimal placement of the needle.
Figure 6:
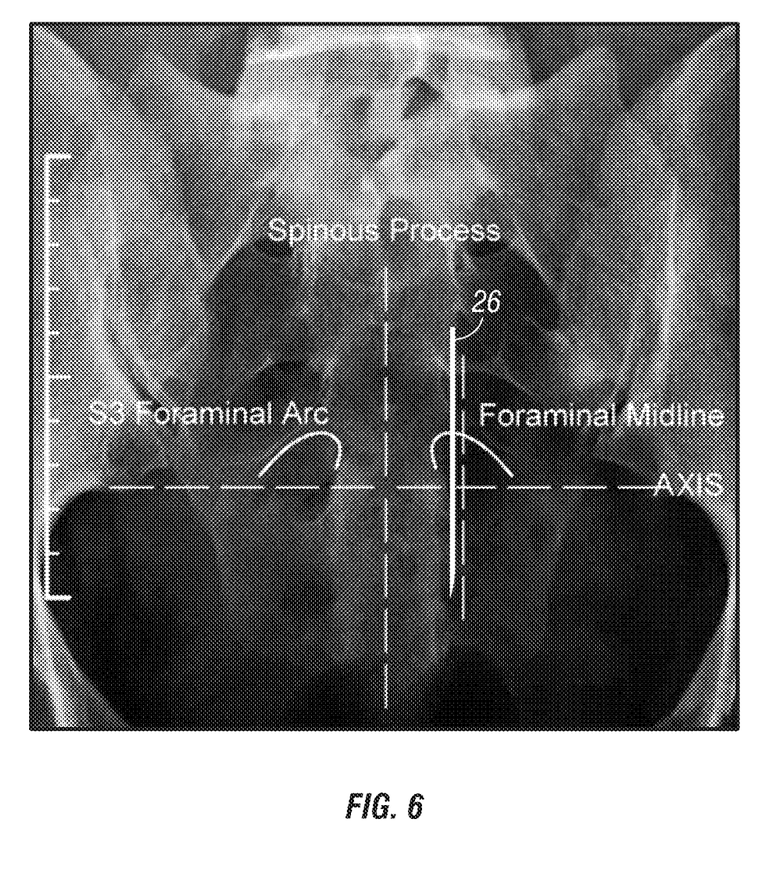
FIG. 6 is an anterior-posterior fluoroscopic image of the sacrum showing optimal placement of the needle.

The practitioner confirms placement of needle 26 in the Anterior/Posterior view for medial placement of needle 26, i.e. approximately parallel to vertical line 42. The practitioner can adjust needle 26 in the Anterior/Posterior and Lateral views until optimal needle placement is achieved in each view. This is shown in FIGS. 5 and 6.

As is known, the practitioner can test needle 26 for optimal placement resulting in the patient experiencing anal bellows and toe flexion at 2 mA or less of stimulation. The practitioner can continue to adjust the needle in the Anterior/Posterior and Lateral views using minute movements and angle changes until the desired result is achieved.

Once this is achieved, the practitioner places the lead into the Sacral #3 foramen according to standard procedure. The practitioner can conduct another test with the lead to ensure the patient experiences anal bellows and toe flexion on all electrodes at 2 mA or less of stimulation. If this is not achieved, the practitioner can remove the lead and begin with needle placement again until the desired response is achieved with the lead.

Figure 7:
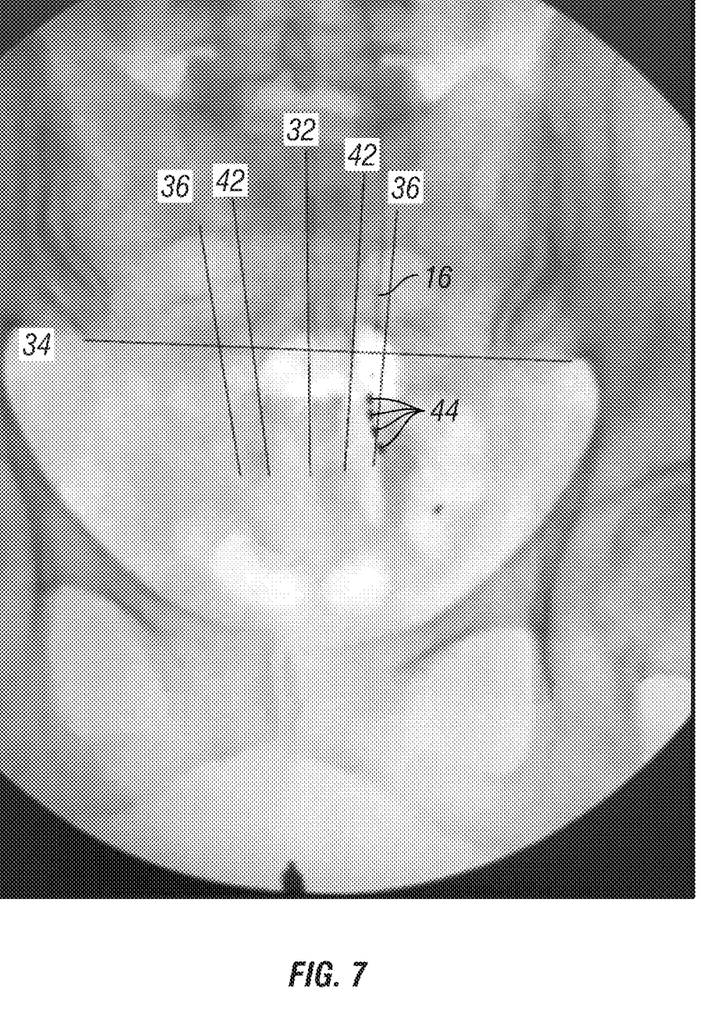
FIG. 7 is an anterior-posterior fluoroscopic image of the sacrum showing lead positioning achieved using the disclosed method.
Figure 8:
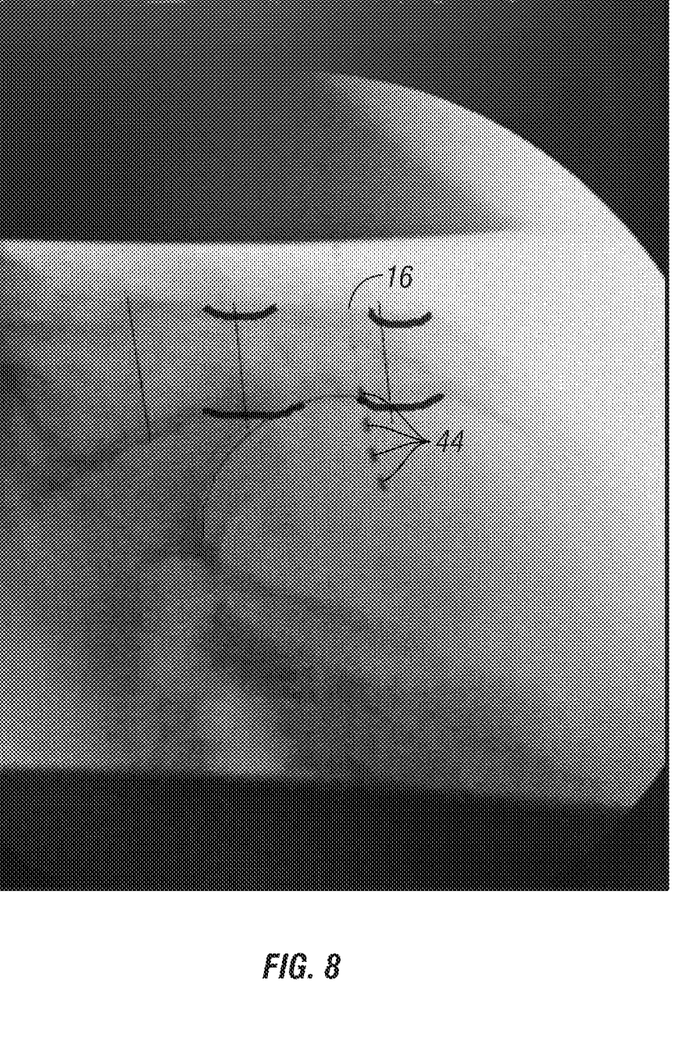
FIG. 8 is a lateral fluoroscopic image of the sacrum showing lead positioning achieved using the disclosed method.

FIGS. 7 and 8 show lead 16 with four electrodes 44 positioned according to the disclosed method.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method for positioning a needle to implant a lead of an electrical stimulator for sacral neuromodulation of a patient, the method comprising:
   fluoroscopically visualizing an anterior/posterior view of the sacrum and sacroiliac joints of the patient;
   marking on the skin of the patient a midline of the sacrum vertically and a horizontal line from one sacroiliac joint to the other sacroiliac joint;
   marking a first point on the horizontal line located a first distance in a first lateral direction from the sacral midline, wherein the first distance approximates a first midline of the desired sacral foramen;
   locating the first midline of the desired sacral foramen using the fluoroscopic anterior/posterior view and the first point and marking the skin of the patient with a first midline vertical line;
   marking the skin of the patient at a second distance and a third distance from the horizontal line superiorly on the first midline vertical line to approximate the desired foramen location;
   marking the skin of the patient with a first medial vertical line representing the approximate medial portion of the first sacral edge using the fluoroscopic anterior/posterior view;
   locating the desired sacral foramen with fluoroscopy in a lateral view;
   placing the needle through the skin at an angle using the skin markings proximate one of the second and third markings, beginning medially at the first midline vertical line and progressing laterally to the first medial vertical line until a distal end of the needle drops into the desired sacral foramen.

2. The method of claim 1, further comprising:
   marking a second point on the horizontal line located the first distance in a second lateral direction from the sacral midline;
   locating a second midline of another desired sacral foramen using the fluoroscopic anterior/posterior view and the second point and marking the skin of the patient with a second midline vertical line, the another desired sacral foramen opposite the desired sacral foramen;
   marking the skin of the patient at the second distance and the third distance from the horizontal line superiorly on the second midline vertical line to approximate the another desired foramen location; and marking the skin of the patient with a second medial vertical line representing the approximate medial portion of the second sacral edge using the fluoroscopic anterior/posterior view.

3. The method of claim 2, wherein the needle angle is approximately 45 degrees.

4. The method of claim 2, wherein the needle angle depends on the body habitus of the patient.

5. The method of claim 2, wherein the placing of the needle is done under fluoroscopic visualization.

6. The method of claim 5, wherein after the distal end of the needle drops into the desired sacral foramen, the angle of the needle is adjusted until the needle is about 1 cm from the inferior edge of the desired sacral foramen and substantially parallel to the inferior edge of the desired sacral foramen.

7. The method of claim 6, further comprising adjusting the angle of the needle using the fluoroscopic anterior/posterior view until the needle is substantially parallel to the first medial vertical line.

8. The method of claim 7, further comprising conducting electricity through the needle to confirm placement of the needle.

9. The method of claim 8, further comprising adjusting the angle of the needle until the patient exhibits a desired response with the conducting of electricity through the needle.

10. The method of claim 1, wherein the first distance is about 2 cm, the second distance is about 4 cm, and the third distance is about 5 cm.

\* \* \* \* \*